United States Patent [19]

Ferres

[11] E Re. 29,650

[45] Reissued May 30, 1978

[54] PHTHALIDE PENICILLIN ESTER INTERMEDIATES

[75] Inventor: Harry Ferres, Horsham, England

[73] Assignee: Beechar Group Limited, Great Britain

[21] Appl. No.: 779,076

[22] Filed: Aug. 18, 1977

Related U.S. Patent Documents

Reissue of:

[64] Patent No.: 3,963,702
Issued: June 15, 1976
Appl. No.: 447,672
Filed: Mar. 4, 1974

U.S. Applications:

[62] Division of Ser. No. 259,560, June 5, 1972, Pat. No. 3,860,579.

[30] Foreign Application Priority Data

June 9, 1971 United Kingdom ..... 19604/71

[51] Int. Cl.[2] ..... C07D 499/32

[52] U.S. Cl. ..... 260/239.1; 424/271

[58] Field of Search ..... 260/239.1

[56] References Cited

U.S. PATENT DOCUMENTS

| | | | |
|---|---|---|---|
| 3,647,783 | 3/1972 | Pirie | 260/239.1 |
| 3,697,507 | 10/1972 | Frederikson et al. | 260/239.1 |

*Primary Examiner*—Gerald A. Schwartz
*Attorney, Agent, or Firm*—Jacobs & Jacobs

[57] ABSTRACT

[The] Phthalide ester of 6-[D(-)α-aminophenylacetamido] penicillanic acid and intermediates therefor. [are described] The phthalide penicillin ester is orally administrable to provide high serum concentrations of the free acid form of the [parent] penicillin.

2 Claims, No Drawings

PHTHALIDE PENICILLIN ESTER INTERMEDIATES

Matter enclosed in heavy brackets [ ] appears in the original patent but forms no part of this reissue specification; matter printed in italics indicates the additions made by reissue.

[This application is a division of application Ser. No. 259,560 filed June 5, 1972, now U.S. Pat. No. 3,860,579.]

*This application is for a Reissue of Pat. No. 3,963,702, granted June 15, 1976, on application Ser. No. 447,672 filed Mar. 4, 1974 as a division of application Ser. No. 259,560 filed June 5, 1972, now U.S. Pat. No. 3,860,579.*

This invention relates to the phthalide ester of 6-[D(−)α-aminophenylacetamido] penicillanic acid and its pharmaceutically acceptable acid addition salts, and to a process for its preparation.

6-[D(−)α-aminophenylacetamido] penicillanic acid is a widely used broad spectrum antibiotic. However, when administered orally, it is incompletely absorbed into the bloodstream. Some medical practitioners believe this to be a disadvantage and consequently some attempts have been made to find derivatives of 6-[D(−)α-aminophenylacetamido] penicillanic acid which will produce higher blood concentrations of the parent penicillin after oral administration than could be achieved with the parent penicillin itself.

It is an object of the present invention to provide a novel ester of 6-[D(−)α-aminophenylacetamido] penicillanic acid which produces high serum concentrations of the parent penicillin when administered orally.

According to the present invention there is provided the phthalide ester of 6-[D(−)α-aminophenylacetamido] penicillanic acid of formula (I), and pharmaceutically acceptable acid addition salts thereof:

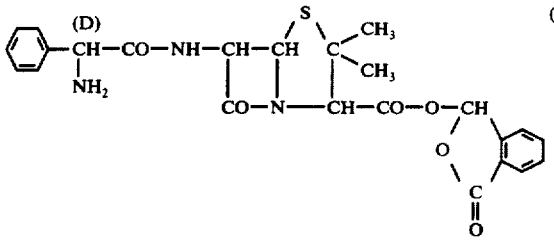

(I)

The preferred acid addition salt of the compound of this invention is the hydrochloride, but salts with other inorganic or organic acids may be used (especially those acids which have been employed to form salts with 6-[D(−)α-aminophenylacetamido] penicillanic acid itself). In addition the compound of this invention will form salts with other penicillanic acids e.g. 3-(2'-chloro-6'-fluorophenyl) 5-methyl-4-isoxazolypenicillin.

The ester of the present invention may be prepared by a process which comprises reacting 6-aminopenicillanic acid phthalide ester or a silyl derivative thereof with reactive N-acylating derivative of the (D) isomer of a compound of formula (II):

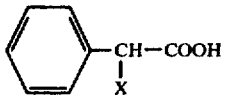

(II)

wherein X is an amino group, a protected amino group or a group which is convertible to an amino group, removing the silyl group, if present, by hydrolysis or alcoholysis, and if X is not an amino group, converting it to such a group under neutral or acid conditions.

By the term "silyl derivative" of the phthalide ester of 6-aminopenicillanic acid we mean the product of the reaction between 6-aminopenicillanic acid phthalide ester and a silylating agent such as a halotrialkylsilane, a dihalodialkylsilane, a halotrialkylsilane, a dihalodialkoxysilane or a corresponding aryl or aralkyl silane and compounds such as hexamethyldisilazane. In general halotrialkylsilanes are preferred, especially trimethylchlorosilane. The silylated derivatives of 6-aminopenicillanic acid phthalide ester are extremely sensitive to moisture and hydroxylic compounds, and after reaction with the reactive derivative of compound (II), the silyl group of the intermediate acylated compound can be removed by hydrolysis or alcoholysis.

In compound (II) the group X is an amino group, protected aino group or a group which is convertible to an amino group.

Examples of protected amino groups include the protonated amino group ($X = NH_3^+$) which, after the acylation reaction can be converted to a free amino group by simple neutralisation; the benzyloxycarbonylamino group ($X = NH.CO_2CH_2Ph$) or substituted benzyloxycarbonylamino groups which are subsequently converted to $NH_2$ by catalytic hydrogenation; and various groups which after the acylation reaction regenerate the amino group on mild acid hydrolysis. (Alkaline hydrolysis is not generally useful since hydrolysis of the phthalide group takes place under alkaline conditions).

Examples of the group X which may subsequently be converted to $NH_2$ by mild acid hydrolysis include enamine groups of general formula (III) or tautomeric modifications thereof, and α-hydroxyarylidene groups of general formula (IV) or tautomeric modifications thereof:

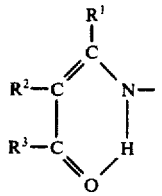

(III)

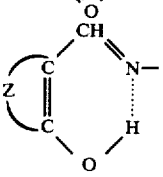

(IV)

In structures (III) and (IV), the dotted lines represent hydrogen bonds. In structure (III) $R^1$ is a lower alkyl group, $R^2$ is either a hydrogen atom or together with $R^1$ completes a carbocyclic ring, and $R^3$ is a lower alkyl, aryl, or lower alkoxy group. In structure (IV) X represents the residue of a substituted or unsubstituted benzene or naphthalene ring.

An example of a group X which can be converted to $NH_2$ after the acylation reaction of the phthalide ester of 6-aminopenicillanic acid with the reactive derivative of (II) is the azido group. In this case, the final conversion into $NH_2$ may be brought about by either catalytic hydrogenation or electrolytic reduction.

A reactive N-acylating derivative of the acid (II) is employed in the above process. The choice of reactive derivative will of course be influenced by the chemical nature of the α-substituent X. Thus, when X is an acid stable group, such as the protonated amino group $NH_3^+$ or the azido group, it is often convenient to convert the acid (II) into an acid halide, for example by treating it with thionyl chloride or phosphorus pentachloride to give the acid chloride.

Such reagents would however be avoided when X is an acid labile group of type (III) or (IV). In such cases it is often convenient to make use of a mixed anhydride. For this purpose particularly convenient mixed anhydrides are the alkoxyformic anhydrides, which are conveniently prepared by treating an alkali metal or tertiary amine salt of the acid (II) with the appropriate alkyl chloroformate in an anhydrous medium at or below room temperature.

Other reactive N-acylating derivatives of the acid (II) include the reactive intermediate formed on reaction in situ with a carbodiimide or carbonyldiimidazole.

The 6-aminopenicillanic acid phthalide ester used in the above process can be prepared, though in poor yield by direct coupling of 6-aminopenicillanic acid with 3-bromophthalide in the presence of a base. With this process some epimerisation at $C_6$ occurs and the process is therefore not entirely satisfactory.

6-Aminopenicillanic acid phthalide ester is also a new compound, and, since it is a valuable intermediate in the process of this invention, it also forms part of the invention. Much better yields of 6-aminopenicillanic acid phthalide ester can be achieved by coupling an N-protected derivative of 6-aminopenicillanic acid (e.g. the triphenylmethyl derivative) with 3-bromophthalide and thereafter removing the protecting group (e.g. by mild acid hydrolysis in the case of the triphenylmethyl derivative).

Alternative types of N-protected 6-amino penicillanic acid are the 6-acylaminopenicillanic acids. Techniques for the removal of the 6-acyl side chain from benzylpenicillin and phenoxymethyl penicillin, for example, are well documented (cf. British Patent No. 1,189,022) and generally involve treating an ester of the 6-acylaminopenicillanic acid with $PCl_5$ to form an imino chloride bond on the 6-amido nitrogen atom, then treating the imino chloride with an alcohol to form an imino ether and then hydrolysing the imino bond to form the 6-aminopenicillanic acid ester. In the present case, it is possible to start from the phthalide ester of penicillin G or penicillin V (prepared for example by reaction of the sodium or potassium salt of the penicillin with 3-bromo phthalide) and cleave the acyl side chain to prepare the phthalide ester of 6-aminopenicillanic acid.

The process described hereinbefore to prepare the phthalide ester of 6-[D(−)α-aminophenylacetamido] penicillanic acid involves acylating the 6-amino group of the 6-aminopenicillanic acid phthalide ester. It is also possible to prepare the compound of this invention by esterification of the 3-carboxyl group of 6-[D(−)α-aminophenylacetamido] penicillanic acid to introduce the phthalido group.

Thus the invention provides in another of its aspects, a method for the preparation of 6[D(−)α-aminophenylacetamido] penicillanic acid phthalide ester of formula (I) above, which process comprises reacting a compound of formula (V):

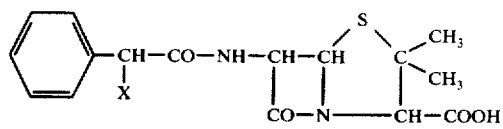

(V)

or a reactive esterifying derivative thereof, in which formula X is as defined with respect to formula (II), with a compound of formula (VI):

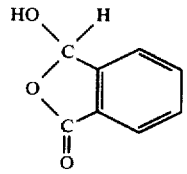

(VI)

or a reactive esterifying derivative thereof, and, if X is not an amino group, subsequently converting it to an amino group under neutral or acid conditions.

By the term "reactive esterifying derivative" in relation to compounds (V) and (VI) above, we mean derivatives of (V) and (VI) which when reacted together take part in a condensation reaction with the consequent formation of an ester linkage:

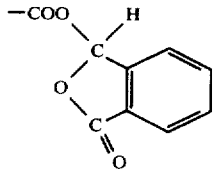

Many methods of esterification using several different combinations of reactive esterifying derivatives of carboxyl and hydroxy groups are known from the literature. For example the esterification reaction defined above may be achieved by reacting a compound of formula (VA):

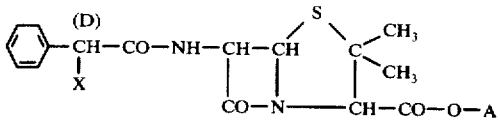

(VA)

wherein x is as defined with respect to formula (II) above, with a compound of formula (VIA):

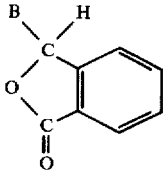

(VIA)

under conditions which cause the elimination of the elements of compound AB with the consequent formation of the ester of formula (VII):

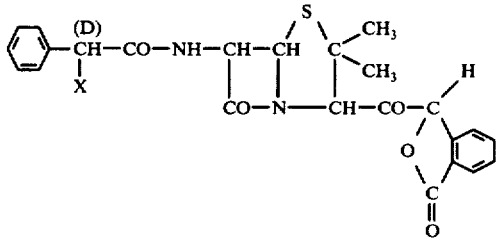

(VII)

and, if X is not an amino group, subsequently converting it to an amino group; the symbols A and B in formulae (VA) and (VI) being such that A represents hydrogen or a salt forming ion and B represents a hydroxy group, an alkylsulphonyloxy group, an arylsulphonyloxy group or a halogen atom or A represents an organic acyl group and B represents a hydroxy group.

It will be clear that these procedures outlined above are all specific applications of esterification methods known in the literature. Although the group X in reagent (V) may be a free amino group, the reaction is best carried out with reagent (V) where X is a protected amino group (preferably an enamine group of formula (III) or a group which can be converted to an amino group (e.g. azido). In such cases it is usually a simple matter to react the sodium or potassium salt of the N-protected compound (V) with compound (VI) wherein B is a halogen atom, especially bromine or chlorine.

In the case of the reaction where the group A in reagent (V) is hydrogen or a salt-forming ion and the group B in reagent (VI) is a hydroxy group, it should be noted that the hydroxy compound (VIB) is in fact in equilibrium as follows:

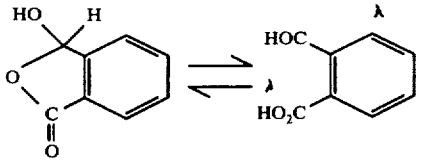

(VIB) (VIII)

and it may in fact be the isomer (VIII) which reacts. However, rather than employ the hydroxy compound (VIB) in this case, we prefer to use the alkylsulphonyl ester or arylsulphonyl ester, since this gives a smoother reaction. In this reaction, the presence of a base is usually necessary to achieve high yields.

In the case where the group A in reagent (V) is an organic acyl group, it will be clear that (V) is simply a mixed anhydride, the acyl group may be one of a wide variety of aliphatic or aromatic acyl groups but generally the alkoxy carbonyl groups (e.g. $C_2H_5OCO$— group) are satisfactory.

Another reactive esterifying derivative of compound (V) above is the acide halide, particularly the acid chloride. This compound may be reacted with the hydroxy compound (VI) in the presence of an acid binding agent to prepare the desired phthalide ester of this invention.

The identity of the various protected amino groups X in formula (V) have already been discussed earlier in this specification with reference to formula (II).

The compound of this invention is well tolerated and is preferably administered orally, optionally in the form of an acid addition salt. Usually it will be administered in combination with suitable pharmaceutically acceptable carriers. In such compositions the compound of this invention may make up between 1% and 95% by weight of the total composition. The composition may be presented as a powder for making up into a syrup, as a tablet, capsule or pill or any other conventional form.

The ester of this invention, or its salts, may conveniently be administered in dosage units containing the equivalent of from 0.025 g to 1 g of 6[D(−)α-aminophenylacetamido] penicillanic acid, preferably the equivalent of from 0.1 to 0.7 g of the penicillanic acid. Dosage units containing the equivalent of 250 mg or 500 mg of the parent penicillanic acid may be found convenient. Daily dosages will depend on the condition of the patient but generally from 1 to 3 g of the ester of this invention (calculated as the parent penicillanic acid) will usually be appropriate.

The compound of this invention — 6[D(−)α-aminophenylacetamido] penicillanic acid phthalide ester — is well absorbed when given to human beings and animals by the oral route. In the serum, high levels of the parent 6[D(−)α-aminophenylacetamido] penicillanic acid are achieved.

The following Examples illustrate the invention:

EXAMPLE 1

(a) 3-Bromophthalide [3-Bromo-1-(3H)-Isobenzofuranone]

Phthalide (10.0 g; 0.075 moles) and N-bromosuccinimide were refluxed in dry carbon tetrachloride (200 ml.) in the presence of a catalytic amount of α-azo-isobutyronitrile for 3–4 hours. The end of the reaction was indicated by the disappearance of N-bromosuccinimide from the bottom of the reaction vessel and the accumulation of succinimide at the top. The succinimide was removed by filtration and the filtrate concentrated in vacuo to 15–20 ml. Cooling of this concentrate followed by filtration gave 13.0 g. (81% yield) of crude 3-bromophthalide, m.p. 75–80°, as a white crystalline solid. The product was recrystallised from cyclohexane as colourless plates, m.p. 78–80° with a 95% recovery. N.m.r. $(CCl_4)_{\overline{Br}}$ δ = 7.67 (4H.m. aromatic), δ = 7.38 (1H.s. CH—)

(b) D(−)α-(aminobenzylpenicillinphthalide ester, hydrochloride

Anhydrous D(−)α-aminobenzylpenicillin (17.5; 0.05 mole) and triethylamine (7.10 ml; 1 equiv.) were mixed with acetone containing 1% of water (2350 ml). After ½ hour potassium bicarbonate (5 g) and 3-bromophthalide (10.65 g; 0.05 mole) were added and the mixture stirred at room temperature for 4 hours. After filtration, the filtrate was concentrated in vacuo to about 75 ml, ethyl acetate (500 ml was added and the resulting solution washed with a 2% aqueous solution of sodium bicarbonate (2 × 100 ml) followed by water (2 × 100 ml). Water (150 ml) was added to the ethyl acetate solution, and, with vigorous stirring, 1N hydrochloric acid was added drop by drop until the pH of the aqueous phase was 2.5. The ethyl acetate layer was separated and dried over anhydrous magnesium sulphate. Ether was then added to the clear yellow ethyl acetate filtrate until no further precipitation of a white amorphous solid occurred. The product was collected (7.8 g; 28.8%). Further material (0.8 g; 3.0%), was obtained from the aqueous layer as follows. To the aqueous layer, n-butanol (750 ml) was added and the resulting mixture was evaporated in vacuo until all the water was removed. The resulting butanolic solution was poured into ether (2000 ml) whereby an amorphous precipitate separated. Combined yields were 31.8%.

The I.R. spectrum (KBr) contains inter alia strong bonds at: 1178 $cm^{-1}$ 1682 $cm^{-1}$ 1500 $cm^{-1}$ 1285 $cm^{-1}$ 1149 $cm^{-1}$ 978 $cm^{-1}$ 752 $cm^{-1}$ 697 $cm^{-1}$ n.m.r. ($(CD_3)_2SO/D_2O$):, $\delta$ = 7.88 (4H.m. phthalide aromatics); $\delta$ = 7.60 (1H.s. —CO.OCH—); $\delta$ = 7.48 (5/6H.m. aromatic); $\delta$ = 5.50 (2H.m. $\beta$-lactams); $\delta$ = 5.16 (1H.s. $\alpha$-proton); $\delta$ = 4.54 (1H.s. $C_3$ proton); $\delta$ = 1.45 (6H.d. gem-dimethyls). The purity as assessed by hydroxylamine and cysteine assays was 92.4% and 86.5% respectively.

$C_{24}H_{24}O_6N_3SCl$ requires: C, 55.65; N, 4.67; N, 8.11; S, 6.19, Cl, 6.84. Found: C, 54.49; H, 4.67; N, 7.83; S, 6.20; Cl, 5.18.

EXAMPLE 2

Phthalide 6-[D(−)α-aminophenylacetamido] penicillanate, Hydrochloride

Method 1

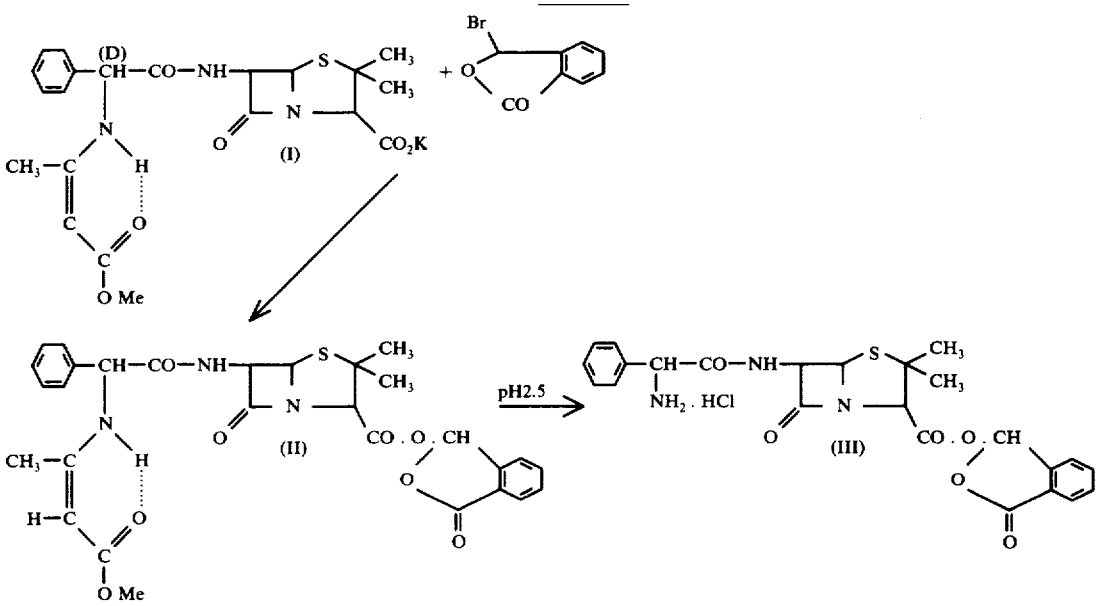

A fine suspension of potassium salt of enamine protected ampicillin I (25.18 g; 0.05 M) and 3-bromophthalide (10.65 g; 0.05 M) were reacted in a 1:2 mixture of acetone/ethyl acetate. (1500 ml) for 24 hours. After filtration the organic layer was washed twice with 250 ml. portions of IN sodium bicarbonate and brine, dried over anhydrous magnesium sulphate and concentrated in vacuo. Addition of ether crystallised the phthalide enamine protected α-aminophenylacetamido penicillanate (II) in 85% yield.

n.m.r. [$(CD_3)_2SO$]; $\delta$ = 7.86 (4H.m. phthalide aromatics); $\delta$ = 7.60 (1H.s. CO.O.CH); $\delta$ = 7.35 (5H.S. aromatics) $\delta$ = 5.30 - 5.65 (3H.m. $\beta$-lactams and $\alpha$-proton); $\delta$ = 4.53 (1H.s. C—3 proton) $\delta$ = 4.50 (1H.s. H) $\delta$ = 3.56 (3H.s. O $CH_3$) $\delta$ = 1.78 (3H.s. $CH_3$) $\delta$ = 1.50 (6H.m. gem di $CH_3$). $C_{28}H_{29}N_3O_8S$ requires: C, 59.26; H, 5.11; N, 7.40 S, 5.68. Found: C, 58.83; H, 5.00; 1N, 6.89 S, 5.34.

Single spot on biochromatogram at $R_f$ = 0.95.

The enamine protecting group was removed from the product (II) by dissolving 10 g. in aqueous acetone (250 ml water to 250 ml acetone) and vigorously stirring this solution at pH 2.5 for 1 hour. The acetone was removed in vacuo and the ester (III), which was salted out of the aqueous phase as a sticky yellow gum, was dissolved in ethyl acetate (200 ml) and washed twice with 200 ml portion, of 1N sodium bicarbonate and brine and dried over anhydrous magnesium sulphate. Careful addition of dry ester (ca.50 ml) to the dry ethyl acetate layer yielded the ampicillin phthalide ester as hydrochloride salt as a fine white amorphous solid in 80% yield.

n.m.r. [$(CD_3)_2SO/D_2O$); $\delta$ = 7.88 (4H.m. phthalide aromatics); $\delta$ = 7.60 (1H.s. CO.O CH—); $\delta$ = 7.48 (5/6H.m. aromatic) $\delta$m = 5.50 (2H.m. $\beta$-lactams); $\delta$ = 51.6 (1H.s. $\alpha$-proton) $\delta$ = 4.54 (1H.s. $C_3$-proton) $\delta$ = 1.45 (6H.d. gem-dimethyls). Purity as assessed by hydroxylamine assay = 110.3%.

Single spot on biochromatogram at $R_f$ = 0.85

$C_{24}H_{24}N_3O_6SCl$ requires: C, 55.65; 1H, 4.67; N, 8.11; S, 6.19. Found C, 54.60; H, 4.70; N, 7.92; S, 6.40.

METHOD 2

A mixture of acetone (250) ml, sodium D(+)N-methoxycarbonylpropen-2-yl-α-aminophenylacetate (30.51g), ethyl chloroformate (10.9ml) and N-methyl morpholine (4–6 drops) were stirred together for 10–15 minutes at −20° to −30° C.

To this solution was added, all at once, a solution of 6-APA (25.4 g) dissolved in water (50ml) with the aid of triethylamine (11.9 g) and then diluted with acetone (150 ml) and cooled to −20° C.

The reaction mixture was stirred for 45 mins. without further cooling and a solution of 3-bromophthalide (25 g) in acetone (100 ml) added all at once, after which stirring was continued for a further 5 hours, the temperature rising meanwhile to ambient (23° C.).

Acetone was next removed in vacuo, after first clarifying the mixture by filtration and to the residue was added ethyl acetate (375 ml.) and 2% sodium bicarbonate solution (200ml.). After stirring for a short while the phases were separated and the organic layer washed again with 2% sodium bicarbonate solution (200 ml).

To the ethyl acetate solution thus obtained was added water (375 ml) and 2N/HCl (60 ml) and this mixture stirred at ambient temperature (23° C) for 45 mins. Petrol (600 ml) was then added and after a short period of stirring the phases were allowed to separate. The organic layer was discarded and the aqueous layer was filtered with a little decolourising charcoal.

Sufficient sodium chloride to saturate the filtrate was next added and after a few minutes stirring the precipitated oil was extracted with methylene dichloride (1 × 400 ml, 1 × 100 ml). These extracts were combined, dried with anhydrous magnesium sulphate, filtered and evaporated under reduced pressure to approximately 100 ml. Ether (500ml) was then added quickly, with stirring to the residue and the resulting precipitate stirred for about 30 mins. at ambient temperature. The product was filtered at the pump, washed with ether (2 × 50 ml) and dried for 3 hours in a forced-air oven at 35° - 40° C. The product was identical with an authenic sample of phthalide 6-[D(−)α-aminophenylacetamido) penicillanate.

EXAMPLE 3

Phthalide 6-aminopenicillanate.

METHOD 1

A mixture of 6-aminopenicillanic acid (10.8 g 0.05 M) and triethylamine (6.9 ml; 0.05 M) was stirred in dry acetone (20 ml) for ½ hour at ambient temperatures. The mixture was cooled to 0° C and a solution of 3-bromophthalide (10.65 g. 0.05 M) in dry acetone (20 ml) added in one portion and the resulting yellow mixture stirred at ambient temperatures for 5 hours. The reaction mixture was diluted with dry diethyl ether (150 ml) and filtered. The clear yellow filtrate was washed with 1N sodium bicarbonate (100 ml) and a saturated brine solution (100 ml). A solution of p-toluenesulphonic acid monohydrate (9.5 g- 1 equiv.) in dry acetone (150 ml) was added to the clear dry yellow filtrate and immediately phthalide epi 6-aminopenicillanate as the p-toluenesulphonate salt crystallised out of solution.

6-α(trans)isomer:

n.m.r.[$(CD_3)_2SO$] :L δ = 7.84 (4H.s. phthalide aromatics); δ = 7.58 (1H.s. CO.O.CH); δ = 7.30 (4H.q. sulphonate aromatics); δ = 5.35 (1H.d. C — 5 proton J = 2Hz); δ = 4.89 (1H.s. C — 3 proton); δ = 4.70 (1H.d. C — 6 proton- J = 2Hz); δ = 2.30 (3H.s. $CH_3$); δ = 1.48 (6H.d. gem-di $CH_3$).

i.r. (KBr disc) strong bands at 1780 $cm^{-1}$, 1210 $cm^{-1}$; 1170 $cm^{-1}$; 1010 $cm^{-1}$; 970 $cm^{-1}$; 682 $cm^{-1}$; 574 $cm^{-1}$.

A residual oil was obtained from the mother liquor from which a small amount (ca. 5%) of a reasonably pure sample of the natural cis isomer of phthalide 6-aminopenicillanate as its p-toluenesulphonate salt was obtained by repeated fractional crystallisation of the 6-α(trans) isomer from an acetone:ether (3:1) solvent mixture.

6-β(cis)isomer:

n.m.r. [$(CD_3)_2SO$]; δ = 7.84 (4H.s. phthalide aromatics) δ = 7.58 (1H.s. CO O CH); δ = 7.30 (4H.q. sulphate aromatics); δ = 5.50 (1H.d. C — 5 proton; J = 4Hz); δ = 5.14 (1H.d. C — 6 proton) J = 4Hz) δ = 4.68 (1H.s. C — 3 proton); δ = 2.27d(3H.s. $CH_3$); δ = 1.53 (6H.d. gem-dimethyls).

i.r. (KBr disc) strong bands at 1780 $cm^{-1}$; 1210 $cm^{-1}$; 1170 $cm^{-1}$; 1010 $cm^{-1}$ 970 $cm^{-1}$ 682 $cm^{-1}$ 574 $cm^{-1}$.

METHOD 2

A solution of 6-tritylaminopenicillanic acid (9.8 g; 0.02M) in dry acetone (100 ml) was cooled to 0° C, triethylamine (2.9 mg, 0.02 M) was added, followed by 3-bromophthalide (4.1 g; 0.02M) in dry acetone (20 ml.), and the reaction mixture kept at 0° C with stirring for 2 hours and finally at ambient temperatures for 1 hour. The triethylammonium bromide which precipitated was removed by filtration, the evaporated filtrate was dissolved in ethyl acetate (150 ml) and after two washings with cold 2% aqueous sodium bicarbonate (2 × 150 ml) and with ice-water (2 × 100 ml) the ethyl acetate layer was dried over anhydrous magnesium sulphate to yield, on removal of solvent in vacuo, phthalide 6-tritylaminopenicillanate as a white amorphous solid.

n.m.r. [$(CD_3)_2SO$]; δ = 7.4 (20 H. broad singlet with smaller shoulder at δ = 7.80 aromatic protons and CO O CH—) S = 4.41 (2H.m. β-lactam protons); δ = 4.15 (1H broad singlet C — 3 proton); δ = 1.38 (6H.d. gem dimethyls).

i.r. (KBrdisc) strong bands at 1745 $cm^{-1}$; 980 $cm^{-1}$ 750 $cm^{-1}$ 708 $cm^{-1}$.

Phthalide 6-tritylaminopenicillanate (5.9 g; 0.01 m) in acetone (200 ml containing 0.2% $H_2O$) was treated with p-toluenesulphonic acid monohydrate (1.9 g; 0.01 M). After standing at room temperature for 2 hours, water (0.25 ml) was added, and the precipitation of phthalide 6-aminopenicillanate p-toluenesulphonate was achieved by the slow addition of petroleum ether, b.p. 40–60° (250 ml). Filtration and consecutive washings with petroleum ether left the crude p-toluenesulphonate salt. The sample was recrystallised from acetone-diethyl ether with an 85% recovery.

n.m.r. [$(CD_3)_2SO$]; δ = 7.84 (4H.s. phthalide aromatics); δ = 7.58 (1H.s. —CO.O CH—); δ = 7.30 (44.9 q. sulphonate aromatics)- β = 5.50 (1H.d. β-lactams; J = 4Hz) δ = 5.14 (1H.d. β-lactam, J = 4Hz); δ = 4.68 (1H.s. C — 3 proton); δ = 2.27 (3H.s. $CH_3$); δ = 1.53 (6H.d. gem dimethyls).

$C_{23}H_{24}N_2S_2O_8$ requires: C, 53.08; H, 4.61; N, 5.39; S, 12.31. Found: C, 52.32 H, 4.60 N, 4.94; S, 12.27.

METHOD 3

Benzylpenicillin phthalide ester:

The potassium salt of benzylpenicillin (20.0 g;10.054 mole) was dissolved in dry dimethylformamide (50 ml) and cooled to 0° C. To this stirred solution 3-bromophthalide (11.5 g; 0.054 mole) in dry dimethylformamide (20 ml) was added in one portion. The reaction mixture was allowed to warm to room temperature and then stirred for a further 2 hours. The mixture was then poured into ice cold water (600 ml) and stirred vigorously. The white solid precipitate which separated was collected and washed well with water. After drying, the material was recrystallised from hot isopropyl alcohol to give a white crystalline product (10.5 g. 41.9%). m.p. 167°–169°. The I.R. spectrum (Nujol) contains inter alia strong bands at: 1770 $cm^{-1}$; 1678 $cm^{-1}$; 1524 $cm^{-1}$ 970 $cm^{-1}$.

n.m.r. [$(CD_3)_2SO/D_2O$] contains peaks at: $\delta$ = 7.88 (4H.m. phthalide aromatics); $\delta$ = 7.61 (1H.s. CO.O CH—); $\delta$ = 7.28 (5H.s. aromatics); $\delta$ = 5.55 (2H.m. $\beta$-lactams); $\delta$ = 4.55 (1H.s. $C_3$ proton); $\delta$ = 3.56 (2H.s. $PhCH_2CO$); $\delta$ = 1.53 (6H.d. gem-dimethyls).

The purity as assessed by hydroxylamine assay was 109.2%.

$C_{23}H_{24}N_2S_2O_8$ requires: C, 53.08; N, 4.61; N, 5.39; S, 12.31. Found: C, 52.50; H, 4.62; N, 4.98; S, 12.34.

EXAMPLE 4

Ampicillin phthalide ester (I) via coupling of phthalide 6-aminopenicillanate with an enamine protected $\alpha$-aminophenylacetic acid mixed anhydride.

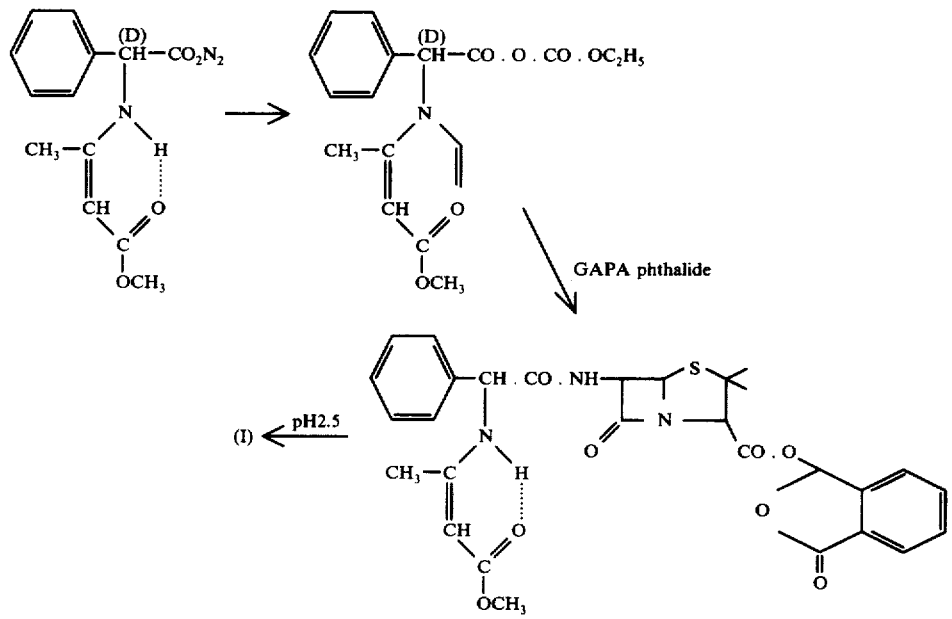

Found C, 61.55; H, 4.90; N, 5.87; S, 6.72; $C_{24}H_{22}N_2SO_6$ requires: C, 61.80; H, 4.72; N, 6.02; S, 6.86.

Benzylpenicillin phthalide ester (11.6 g; 0.025M) was dissolved in dry methylene dichloride (250 ml) and chilled to −25°. N-methyl morpholine (5.60 ml; 0.025M) was added followed by a solution of phosphorus pentachloride (6.0 g) in methylene dichloride (150 ml.) over 5 minutes. A pale yellow colour developed and after stirring for ½ hour the temperature rose to 0°. The reaction mixture was recooled to −25° and N-methylmorpholine (5.60 ml) and dry methanol was added to give a slow steady rise in temperature to ca −10°.

After stirring at −5° to 0° for a further 2 hours water (400 ml) was added with vigorous stirring whilst the pH of the mixture was adjusted from 1.2 to 6.0 with dilute sodium hydroxide solution.

The organic phase was separated washed with water and saturated brine and filtered through siliconised paper.

A solution of p-toluenesulphonic acid monohydrate (4.75 g 0.025M) in acetone (100 ml) was added with stirring to the organic layer and ether added until the solution appeared cloudy. On standing overnight at 0°, 7.0 g of white crystalline 6-aminopenicillanic acid phthalide ester, p-toluenesulphonate was obtained and a further crop of 2.5 g obtained by concentration of the filtrate. Total yield = 9.5 g 73.4%.

n.m.r. [$(CD_3)_2SO$] $\delta$ = 7.84 (4H.s. phthalide aromatics); $\delta$ = 7.58 (1H.s. —CO.O CH) $\delta$ = 7.30 (4H.s. sulphonate aromatics) $\delta$ = 5.50 (1H.d. $\beta$-lactam J = 4Hz) $\delta$ = 5.14 (1H.d. $\beta$ lactam. J = 4Hz) $\delta$ = 4.68 (1H.s. $C_3$ proton) $\delta$ = 2.27 (3H.s. $CH_3$—) $\delta$ = 1.53 (6H.d. gem di-$CH_3$).

Phthalide 6-aminopenicillanate p-toluenesulphonate (10.4 g) was suspended in ethyl acetate (60 ml) and stirred vigorously with 1N-sodium bicarbonate (135 ml) for 20 min. at ambient temperatures. The organic layer was separated, washed with water (100 ml) containing 2% sodium bicarbonate (5 ml) and dried over anhydrous magnesium sulphate, filtered and kept at −15° C.

A mixed anhydride of sodium D(−)N-(1-methoxycarbonylpropen-2-yl)-$\alpha$-aminophenylacetate (5.4 g) in ethyl acetate (30 ml) was prepared by the addition of ethyl chloroformate (2 ml) and pyridine (2 drops) at −15° and stirring the reaction mixture for 10 min. at −15° to −20° C. To this mixed anhydride solution was added the ethyl acetate solution of phthalide 6-aminopenicillanate and the mixed stirred at −15° for 15 mins. and then for a further 45 min. without further cooling.

Water (75 ml) was added, followed by 2N-hydrochloric acid (10 ml) and the reaction mixture stirred vigorously for 25 mins. Petroleum ether, b.p. 60–80° (250 ml) was added slowly with stirring. The aqueous layer was separated and saturated with sodium chloride and the oil which separated was extracted into ethyl acetate (2 × 100 ml) and dried over anhydrous magnesium sulphate.

After filtration, the solution was concentrated in vacuo to ca ¼ volume, dry ether (ca. 250 ml) was added slowly and the ampicillin phthalide which precipitated as a white amorphous hydrochloride salt (4.0 g; 40%) was collected and washed well with ether. Hydroxylamine assay = 76.1% Iodometric assay = 77.5% chlorine content = 7.07% (theoretical = 6.85%).

EXAMPLE 5

6-Aminopenicillanic acid (18.5 g- 0.085 mole) and sodium bicarbonate (21g; 0.25 mole) were dissolved in 200 ml of water and 100 ml of acetone. To this solution, chilled in ice, was added α-azidophenylacetyl chloride (16.6 g; 0.085 mole) diluted with 10 ml of dry acetone. The temperature was held at 0° to 5° C and the reaction mixture stirred for 2.5 hours.

The pH of the mixture was adjusted to 7.5 by adding a saturated sodium bicarbonate solution. After being washed twice with diethyl ether, the reaction solution was acidified to pH 2 with dilute HCl, and extracted with ether. The ether solution containing the free penicillin was washed twice with water and then extracted with 50 ml of N potassium bicarbonate solution. After freeze drying the potassium salt of α-azidobenzyl penicillin was obtained as a white powder (2944 g; 84% yield).

The potassium salt of α-azidobenzyl penicillin (21.53 g; 0.05 mole) was dispersed in methylene dichloride (250 ml) and acetone (100 ml) and the mixture chilled to −5° C. To the stirred suspension ethyl chloroformate (5.13 g- 0.048 mole) was added dropwise followed by a catalytic quantity of pyridine. The mixture was stirred at −5° C for 30 minutes.

O-Phthalaldehydic acid (6.5 g; 0.05 mole) was then added to the reaction mixture and after a few minutes, the cooling bath was removed and the temperature was allowed to rise to ambient temperature. The reaction was continued with constant stirring for a further 3 hours. The reaction mixture was then filtered and the filtrate concentrated to low volume by evaporation in vacuo. Lyophilisation gives the crude phthalide ester of α-azidobenzylpenicillin.

Catalytic hydrogenation of the crude phthalide ester of α-azidobenzylpenicillin gave the phthalide ester of α-aminobenzylpenicillin which, after purification by chromatography was found to be identical with an authentic sample prepared by the method of Example 2.

EXAMPLE 6

The rates of hydrolysis of the phthalide ester of 6-[D(−)α-aminophenylacetamido penicillanic acid HCl were determined by incubating the ester at the equivalent of 5μg/ml 6-[D(−)α-aminophenylacetamido] penicillanic acid in M/20 pH 7.0 potassium phosphate buffer, 90% human blood and 90% squirrel monkey blood. The ester was also tested for hydrolysis in squirrel monkey small intestine homogenate at the equivalent of 100 μg/ml 6-[D(−)α-aminophenylacetamido] penicillanic acid, the reaction mixtures being diluted to the equivalent of 5.0 μg/ml of the parent penicillanic acid before assay. The tissue homogenate was prepared by homogenising washed squirrel monkey small intestine in four times its weight of M/20 potassium phosphate buffer. This stock preparation was diluted a further 1:10 for the reaction mixture.

All reaction mixtures were incubated at 37° C. After incubation, the ester was separated from the reaction mixture by electrophoresis. 5 μl. aliquots of the reaction mixtures, and 6-[D(−) α-aminophenylacetamido] penicillanic acid standards prepared in the appropriate medium, were applied to starch-agar gel plates buffered at pH 5.5. A potential of 15 volts/cm was applied across the plate for 20 minutes. At this pH the parent penicillanic acid remains near the origin and any ester present migrates towards the cathode. The amount of parent penicillanic acid present in the reaction mixtures was assayed by overlayering the gel plates with nutrient agar (Oxoid blood base agar) seeded with Sarcina lutea NCTC 8340, and incubating for 16 hours at 30° C. Zones of inhibition, resulting from ampicillin in test samples and standards, were measured, and the amount of parent penicillanic acid formed in the reactions calculated.

RESULTS

| Hydrolysis Medium | % Hydrolysis at 37° C to 6-[D(−)α-aminophenylacetamido] Penicillanic acid at: 3 mins | 8 mins | 15 mins | 25 mins |
|---|---|---|---|---|
| Acid (pH 2.0) | 0 | 0 | 0 | 0 |
| Aqueous Buffer pH 7.0) | 10 | 15 | 20 | 25 |
| Human Blood (pH 7.0) | 50 | 62 | 80 | 84 |
| Squirrel Monkey Blood (pH 7.0) | 78 | 84 | 90 | 100 |
| Squirrel Monkey Small Intestine | 80 | 84 | 92 | 100 |

I claim:

1. A compound of the formula:

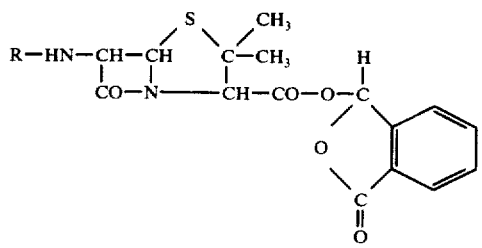

wherein R is hydrogen or

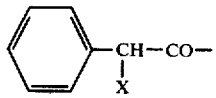

in which X is [$NH_3^+$,] benzyloxycarbonylamino, $N_3$ or an enamine of the formula:

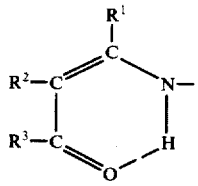

wherein $R^1$ is lower alkyl, $R^2$ is H, $R^3$ is lower alkyl, lower alkoxy or phenyl, or $R^2$ together with $R^1$ completes a fused 5- or 6 membered carbocyclic ring.

2. The compound of claim 1 in which R is hydrogen.

* * * * *

UNITED STATES PATENT AND TRADEMARK OFFICE

CERTIFICATE OF CORRECTION

PATENT NO. : Reissue 29,650
DATED : May 30, 1978
INVENTOR(S) : Harry Ferres

It is certified that error appears in the above-identified patent and that said Letters Patent are hereby corrected as shown below:

IN THE HEADING:

[73] "Beechar" is changed to -- Beecham --

[22] "Aug. 18, 1977" is changed to -- March 18,1977--

Signed and Sealed this

*Twenty-fourth* Day of *October 1978*

[SEAL]

*Attest:*

RUTH C. MASON
*Attesting Officer*

DONALD W. BANNER
*Commissioner of Patents and Trademarks*